United States Patent [19]

Taglieber et al.

[11] Patent Number: 4,929,759

[45] Date of Patent: May 29, 1990

[54] PRODUCTION OF AMINES FROM AN OLEFIN AND AMMONIA OR A PRIMARY OR SECONDARY AMINE

[75] Inventors: Volker Taglieber, Eppelheim; Wolfgang Hoelderich, Frankenthal; Rudolf Kummer, Frankenthal; Wolf D. Mross, Frankenthal; Guenter Saladin, Ludwigshafen, all of Fed. Rep. of Germany

[73] Assignee: BASF Aktiengesellschaft, Ludwigshafen, Fed. Rep. of Germany

[21] Appl. No.: 418,939

[22] Filed: Oct. 6, 1989

Related U.S. Application Data

[63] Continuation of Ser. No. 273,160, Nov. 18, 1988, abandoned, Continuation of Ser. No. 5,339, Jan. 15, 1987, abandoned, Continuation of Ser. No. 633,281, Jul. 23, 1984, abandoned.

[51] Int. Cl.$^5$ .............................................. C07C 85/18
[52] U.S. Cl. ................................... 564/485; 564/408; 564/445
[58] Field of Search ............... 564/395, 408, 445, 469, 564/478, 485; 502/71, 77

[56] References Cited

U.S. PATENT DOCUMENTS

| | | | |
|---|---|---|---|
| 2,422,631 | 6/1947 | Olin et al. | 263/583 |
| 2,501,556 | 3/1950 | Whitman | 260/563 |
| 2,623,061 | 12/1952 | Teter et al. | 260/465.3 |
| 3,210,267 | 10/1965 | Plank et al. | 208/120 |
| 3,271,418 | 9/1966 | Plank et al. | 208/120 |
| 3,412,158 | 11/1968 | McClain | 260/585 |
| 3,594,311 | 7/1971 | Frilette et al. | 208/111 |
| 3,769,202 | 10/1973 | Plank et al. | 208/111 |
| 4,001,106 | 1/1977 | Plank et al. | 208/75 |
| 4,111,840 | 9/1978 | Best | 564/480 |
| 4,268,420 | 5/1981 | Klotz | 252/432 |
| 4,269,813 | 5/1981 | Klotz | 423/277 |
| 4,292,457 | 9/1981 | Klotz | 585/447 |
| 4,292,458 | 9/1981 | Klotz | 585/469 |
| 4,307,250 | 12/1981 | Peterson | 564/445 |
| 4,327,236 | 4/1982 | Klotz | 585/481 |
| 4,427,577 | 1/1984 | Koetsier | 502/74 |
| 4,431,746 | 2/1984 | Rollmann | 502/77 |

FOREIGN PATENT DOCUMENTS 2746790 4/1978 Fed. Rep. of Germany .
1074130 6/1967 United Kingdom .

OTHER PUBLICATIONS

K. G. Ione et al., J. Mol. Catal., 31, 355–370 (1985).
W. Hoelderich et al., Aluminosilicate and Borosilicate Zeolites and Their Use the Conversion of Methanol to Olefins, Proc. of the 6th Inter. Zeolite Conf. (Jul. 1983).
Kokotailo et al., "The Properties and Application of Zeolites", Special Pub. of Chem. Soc. of London #33, (1979).
Xu, et al. "ZSM-5 Molecular Sieves Containing Boron", Chemical Abstracts vol. 99:219187u, (1982).
Hoelderich et al., "Niobium Containing Alumino-and Borosilicate Zeolites", Chemical Astracts vol. 99:178340t (1983).
Gabelica et al., "Synthesis and Characterization of Pentasil-Type Zeolites", CA 98:144326q (1981).

Primary Examiner—Richard L. Raymond
Assistant Examiner—Peter G. O'Sullivan
Attorney, Agent, or Firm—Keil & Weinkauf

[57] ABSTRACT

Amines are prepared from an olefin and ammonia or a primary or secondary amine, or a mixture of these, in the presence of a borosilicate or borogermanate zeolite of the pentasil type as a catalyst, by a process in which the amine obtained is isolated from the reaction mixture, and unreacted starting materials are recycled.

14 Claims, No Drawings

PRODUCTION OF AMINES FROM AN OLEFIN AND AMMONIA OR A PRIMARY OR SECONDARY AMINE

This application is a continuation of application Ser. No. 273,160, filed on Nov. 18, 1988, now abandoned, which is a continuation of application Ser. No. 005,339 filed on Jan. 15, 1987, now abandoned, which is a continuation of Ser. No. 633,281 filed on July 23, 1984, now abandoned.

The present invention relates to a process for the preparation of amines by an addition reaction of ammonia, or of an amine which reacts in a similar manner, with an olefin.

The addition reaction of ammonia, or of an amine which reacts in a similar manner, with an olefin has long been known and has frequently been described. To date, the reaction has not been realized industrially since the conventional processes give inadequate selectivities and/or catalyst lives, as described in, for example, U.S. Pat. Nos. 2,623,061, 2,422,631, 2,501,556 and 3,412,158. The process described in U.S. Pat. No. 4,307,250 also cannot be carried out on an industrial scale. The aluminosilicate zeolites which are used as catalysts promote substantial polymer formation and subsequent coking, which results in rapid deactivation of the catalyst.

We have found that, in the preparation of amines from an olefin and ammonia or a primary or secondary amine at from 80° to 400° C. and under from 40 to 700 bar in the presence of a zeolite catalyst, the catalyst used has a long life and high selectivity if an olefin is reacted with ammonia or a primary or secondary amine, or a mixture of these, in the presence of a borosilicate or borogermanate zeolite of the pentasil type as a catalyst, the resulting amine is isolated and the unreacted starting materials are recycled.

A feature of the novel process is that even a small excess of ammonia or amine is sufficient to give the desired product with high selectivity and to avoid dimerization and/or oligomerization of the olefin used.

In an embodiment of the process, ammonia and/or the amines are mixed with the olefin in a molar ratio of from 1:1 to 5:1, and the mixture is fed to a fixed bed or fluidized bed reactor and reacted under from 40 to 700, in particular from 200 to 300 bar and at from 80° to 400° C., in particular from 250° to 350° C., in the gas phase or in a supercritical state. In another embodiment, the reaction is carried out in the liquid phase under from 40 to 80 bar and at from 60° to 120° C. in a stirred kettle, a solid/liquid fluidized bed or a flow tube. The desired product is obtained from the reaction mixture by a conventional method, for example distillation or extraction, and, if necessary, is brought to the desired purity by further separation operations. The unreacted starting materials are recycled to the reactor.

Monounsaturated or polyunsaturated olefins of 2 to 10 carbon atoms, or mixtures of these, can be used as starting materials. Because of the lower tendency to undergo polymerization, monoolefins are more suitable than diolefins or polyolefins, although these can also be reacted selectively with the aid of a larger excess of ammonia or amine. The position of the equilibrium, and hence the conversion to the desired amine, depends to a very great extent on the reaction pressure chosen. High pressure favors the adduct, but, for technical and economic reasons, the optimum pressure is no higher than 300 bar. Apart from being affected by factors such as the excess amount of ammonia or amine, and the catalyst, the selectivity of the reaction is influenced to a large extent by the temperature. Although the rate of the addition reaction increases sharply with increasing temperature, competing crack and recombination reactions of the olefin are promoted at the same time. The optimum temperature with regard to conversion and selectivity depends on the constitution of the olefin, of the amine employed and of the catalyst, and is in general from 250° to 350° C. The residence time depends on the starting materials, and is advantageously from a fraction of a second to a few minutes.

The catalysts used for the amination of olefins are borosilicate or borogermanate zeolites of the pentasil type.

Suitable borosilicate and borogermanate zeolites are synthesized at from 90° to 170° C. under autogenous pressure, by reacting a boron compound, eg. $H_3BO_3$, with a silicon compound or a germanium compound, preferably highly disperse silicon dioxide or germanium oxide, in an aqueous amine solution, in particular in 1,6-hexanediamine solution, 1,3-propanediamine solution or triethylenetetramine solution, with or without the addition of an alkali or alkaline earth metal.

Such borosilicate or borogermanate zeolites can also be obtained if the reaction is carried out in solution in ether, eg. diethylene glycol dimethyl ether, or in alcohol, eg. methanol or butane-1,4-diol, instead of in an aqueous amine solution.

After the resulting borosilicate or borogermanate zeolites have been isolated, dried at from 100° to 160° C., preferably about 110° C., and calcined at from 450° to 550° C., preferably about 500° C., they can be mixed with a binder in a weight ratio of from 90:10 to 40:60 and then converted to extrudates or tablets. Suitable binders are various aluminas, preferably boehmite, amorphous aluminosilicates having an $SiO_2/Al_2O_3$ ratio of from 25:75 to 95:5, silicon dioxide, preferably highly disperse $SiO_2$, mixtures of highly disperse $SiO_2$ and highly disperse $Al_2O_3$, highly disperse $TiO_2$, and clay. After the molding procedure, the extrudates or pellets are advantageously dried at 110° C. for 16 hours and calcined at 500° C. for 16 hours.

In a particular embodiment, the borosilicate or borogermanate zeolite isolated is molded directly after the drying procedure, and is subjected to calcination only after molding has been carried out.

By milling and sieving the catalyst extrudates, it is possible to obtain fluidizable material from 0.1 to 0.8 mm in size.

When the zeolite catalyst has been deactivated by coking during the reaction according to the invention, the catalyst can be regenerated in a simple manner by burning off the coke deposit in air or in an air/$N_2$ mixture at from 400° to 550° C., preferably about 500° C. As a result of this procedure, the catalyst regains its initial activity.

To increase the selectivity, the catalyst life and the number of regenerations possible, the zeolite catalysts can be modified in a number of different ways.

In one possible method of modifying the catalysts, the unmolded zeolites or the zeolite moldings are doped or subjected to an ion exchange reaction with an alkali metal, eg. Na or K, an alkaline earth metal, eg. Ca or Mg, an earth metal, eg. Tl, a transition metal, eg. Mn, Fe, Mo, Cu or Zn, or a rare earth metal, eg. La or Ce.

In an advantageous embodiment, the pentasil zeolite moldings are initially taken in a flow tube and, for example, a halide or a nitrate of one of the metals described above is passed over at from 20° to 100° C. Ion exchange of this type can be carried out, for example, on the hydrogen, ammonium or alkali metal form of the zeolite.

Another possible method of introducing the metal onto the zeolite comprises impregnating the zeolite material with, for example, a halide, a nitrate or an oxide of one of the metals described above, in aqueous or alcoholic solution.

Both ion exchange and impregnation can be followed by a drying step and, if desired, repeated calcintion. In the case of metal-doped zeolites, after-treatment with hydrogen and/or steam may be advantageous.

Another possible method of modification comprises treating the zeolite material, in either molded or unmolded form, with an acid, eg. hydrochloric acid, hydrofluoric acid or phosphoric acid.

In a particular embodiment, the zeolite powder, before being molded, is refluxed with 0.001–2N, preferably 0.05–0.5N, hydrofluoric acid for from 1 to 3 hours. The product is filtered off, washed, dried at from 100° to 160° C. and then calcined at from 400° to 550° C. Another particular embodiment comprises molding the zeolite together with a binder and then treating the moldings with HCl. In this procedure, the zeolite is treated with from 3 to 25, in particular from 12 to 20, % strength hydrochloric acid for from 1 to 3 hours at from 60° to 80° C., and the product is then washed, dried at from 100° to 160° C. and calcined at from 400° to 550° C.

Another possible method of modification comprises exchange with an ammonium salt, eg. NH$_4$Cl, or with a mono-, di- or polyamine. In this procedure, the zeolite, which has been molded with a binder and is present in the H form or in a different ammonium form, is subjected to continuous exchange with from 10 to 25, preferably 20, % strength NH$_4$Cl solution for 2 hours at from 60° to 80° C., the weight ratio of zeolite to ammonium chloride solution being 1:15, and the product is then dried at from 100° to 120° C.

For the amination of the olefins, the catalysts can be used in the form of 2–4 mm extrudates, tablets having a diameter of from 3 to 5 mm, fluidizable material from 0.1 to 0.8 mm in size, or grit having a diameter of from 0.5 to 1 mm.

The Examples which follow illustrate the invention.

EXAMPLE 1

Catalyst A is prepared, by a hydrothermal synthesis, from 64 g of SiO$_2$ (highly disperse silica), 12.2 g of H$_3$BO$_3$ and 800 g of an aqueous 1,6-hexanediamine solution (weight ratio 50:50) in a stirred autoclave under autogenous pressure and at 170° C. The crystalline product is filtered off, washed, dried at 110° C. for 24 hours and then calcined at 500° C. for 24 hours. The resulting borosilicate zeolite of the pentasil type contains 94.2% by weight of SiO$_2$ and 2.32% by weight of B$_2$O$_3$.

This zeolite is converted to 2 mm extrudates by molding with boehmite in a weight ratio of 60:40, and the extrudates are dried at 110° C. for 16 hours and calcined at 500° C. for 24 hours.

Catalyst B is prepared by refluxing 50 g of the borosilicate zeolite described above with 140 ml of 0.1N HF for 1 hour. The product is filtered off, washed with water, dried at 110° C. for 16 hours and calcined at 500° C. for 5 hours. It is mixed with boehmite in a ratio of 60:40, the mixture is converted to extrudates, and the latter are dried at 110° C. for 16 hours and calcined at 500° C. for 16 hours.

Catalyst C is obtained by subjecting catalyst A to a ion exchange reaction with an Na compound at room temperature, so that the catalyst contains 0.32% by weight of Na after washing out with water and drying at 110° C. for 16 hours.

10 ml of catalyst A, B or C described above are introduced into a 0.3 liter stirred autoclave, the autoclave is closed and the olefins and ammonia or amines are forced in. The amount of starting material is such that the autogenous pressure of the reactants at the reaction temperature chosen corresponds to the desired pressure. The molar ratio of ammonia or amine to olefin is varied from 1:1 to 5:1, and the reaction time is fixed at 30 minutes.

The liquid phase and the gas phase of the reacted mixture are investigated separately by gas chromatography. The conversions shown in Table 1 are based in each case on the olefin; the stated selectivities are based on the principal products: ethylamine from ethylene, isopropylamine from propylene, isobutylamine from but-1-ene, tert.-butylamine from isobutene, isopentylamine from isobutene and methylamine, and 1-amino-4-(1-aminoethyl)-cyclohexane from 4-vinyl-1-cyclohexene.

TABLE 1

| Olefin | Amine | Molar ratio amine:olefin | Catalyst | Temperature [°C.] | Pressure [bar] | Conversion [%] | Selectivity [%] |
|---|---|---|---|---|---|---|---|
| Ethylene | NH$_3$ | 2:1 | A | 350 | 295 | 4.7 | 97.8 |
| " | " | " | A | 370 | 305 | 7.3 | 94.0 |
| " | " | " | C | 370 | 290 | 6.9 | 95.2 |
| Propylene | " | 1.5:1 | A | 330 | 285 | 9.2 | 96.4 |
| " | " | " | A | 350 | 290 | 11.3 | 97.8 |
| " | " | " | C | 330 | 270 | 10.1 | 95.9 |
| " | " | 3:1 | C | 350 | 305 | 11.7 | 94.7 |
| But-1-ene | " | 1.5:1 | A | 330 | 300 | 10.9 | 98.2 |
| Isobutene | " | " | A | 300 | 280 | 12.3 | 97.2 |
| " | " | " | A | 330 | 570 | 13.7 | 98.5 |
| " | " | " | A | 350 | 295 | 14.1 | 95.7 |
| " | " | " | B | 330 | 300 | 13.9 | 96.8 |
| " | " | " | C | 330 | 275 | 13.1 | 97.4 |
| " | CH$_3$NH$_2$ | 2:1 | A | 330 | 235 | 9.3 | 93.2 |
| 4-Vinyl-1-cyclohexene | NH$_3$ | 4:1 | A | 330 | 260 | 8.7 | 87.6 |

EXAMPLE 2

Continuous preparation is carried out using a high pressure reactor which has a length of 2 m and an internal diameter of 24 mm, is heated by means of an aluminum block and is equipped for internal temperature measurement at three points and with a pressure regulator. 60 ml of each catalyst are introduced, and the upper part of the reactor tube is filled with porcelain rings. The olefin and amine are fed in from above.

The reacted mixtures are analyzed by gas chromatography and in some cases by distillation.

The results obtained with the various catalysts are shown in Table 2. Some of the results were obtained with intermediate regeneration of the catalyst. Analysis of the catalyst removed after 28 days' operation gives a carbon content of 11.0%.

converted over the catalysts A, B, C, D, E, F and G under isothermal conditions at 300° C. and under 300 bar, a batchwise procedure being employed. The products are analyzed by gas chromatography.

The experimental results are summarized in Table 3.

TABLE 3

| Catalyst | A | A | B | C | D | E | F | G |
| --- | --- | --- | --- | --- | --- | --- | --- | --- |
| Temperature (°C.) | 300 | 300 | 300 | 300 | 300 | 300 | 300 | 300 |
| Pressure (bar) | 300 | 300 | 300 | 300 | 300 | 300 | 300 | 300 |
| GHSV (liter of educt per g of catalyst per hour) | 4 | 6.5 | 4.5 | 10 | 15 | 3.3 | 11 | 3.3 |
| Conversion of isobutene (%) | 13.1 | 12.8 | 14.5 | 13.6 | 7.8 | 13.6 | 17.3 | 15.0 |
| Selectivity with respect to tert.-butylamine (%) | 96.9 | 96.6 | 95.7 | 96.9 | 92.2 | 95.5 | 97.3 | 97.8 |

TABLE 2

| Olefin | Amine | Molar ratio amine:olefin | Catalyst | Space velocity (kg per liter of catalyst per hour) | Temperature (°C.) | Pressure (bar) | Conversion (%) | Selectivity (%) | STY (kg per liter of catalyst per hour) |
| --- | --- | --- | --- | --- | --- | --- | --- | --- | --- |
| Propylene | NH$_3$ | 1.5:1 | A | 3 | 350 | 300 | 7.8 | 98.7 | 0.23 |
| " | " | " | A | 9 | 350 | 300 | 5.3 | 98.3 | 0.47 |
| " | " | " | A | 18 | 350 | 300 | 3.9 | 99.0 | 0.70 |
| " | " | " | A | 9 | 370 | 300 | 6.4 | 96.4 | 0.55 |
| Isobutene | " | " | A | 9 | 300 | 300 | 5.4 | 99.7 | 0.38 |
| " | " | " | A | 9 | 310 | 300 | 8.6 | 99.8 | 0.65 |
| " | " | " | A | 9 | 320 | 300 | 6.3 | 99.6 | 0.33 |
| " | " | " | A | 18 | 350 | 300 | 4.7 | 98.0 | 0.69 |
| " | " | " | A | 9 | 320 | 200 | 4.9 | 99.4 | 0.26 |

STY = space-time yield for isopropylamine or tert.-butylamine

Catalyst D is obtained by refluxing 50 g of catalyst A with 250 ml of 15% strength hydrochloric acid for 1 hour, filtering off the product, washing it Cl-free, drying it at 110° C. for 16 hours and calcining it at 500° C. for 5 hours.

Catalyst E is prepared by impregnating 50 g of catalyst A with 9.4 g of Zn(NO$_3$)$_3$.6H$_2$O and then calcining the product at 540° C. for 2 hours.

Catalyst F is obtained by combining the borosilicate zeolite described in Example 1 with a mixture of highly disperse SiO$_2$ and Al$_2$O$_3$ (Al$_2$O$_3$ content=3.5% by weight) in a weight ratio of 60:40, converting the mixture to extrudates, and drying the extrudates at 110° C. for 16 hours and calcining them at 500° C. for 16 hours.

Catalyst G is obtained by combining the borosilicate zeolite described in Example 1 with a mixture of 90% by weight of highly disperse SiO$_2$ and 10% by weight of boehmite in a weight ratio of 60:40, converting the mixture to extrudates, and drying the extrudates at 110° C. for 16 hours and calcining them at 500° C. for 16 hours.

In a tube reactor (6 mm internal diameter), a mixture of isobutene and ammonia in a molar ratio of 1:1.3 is

We claim:

1. A process for the preparation of an amine from an olefin and ammonia or a primary or secondary amine at from 80° to 400° C. and under from 40 to 700 bar in the presence of a zeolite catalyst, wherein an olefin is reacted with ammonia or a primary or secondary amine, or a mixture of these, in the presence of a borosilicate or borogermanate zeolite of the pentasil type as a catalyst, the resulting amine is isolated and the unreacted starting materials are recycled.

2. The process as claimed in claim 1, wherein the catalyst is molded together with a binder and then calcined.

3. The process of claim 1, wherein the catalyst is treated with an acid.

4. The process of claim 1, wherein the catalyst is doped with a transition metal.

5. The process of claim 1, wherein the catalyst is doped with a rare earth.

6. The process of claim 1, wherein the catalyst is doped with an alkali metal, an alkaline earth metal and/or an earth metal.

7. The process of claim 1, wherein the catalyst is treated with an ammonium salt and then used in its ammonium form.

8. A process for preparing an amine, which comprises the steps of:
   (a) reacting
   (i) an olefin with
   (ii) ammonia, a primary amine, a secondary amine or a mixture thereof, in the presence of a borosilicate zeolite catalyst of the pentasil type at from 250° to 350° C. and under 40 to 700 bar;
(b) isolating the amine product; and
(c) recycling unreacted materials (i) and (ii).

9. The process of claim 8, wherein the reaction is carried out at from 200 to 300 bar.

10. The process of claim 8, wherein the borosilicate pentasil zeolite catalyst is doped with an alkaline metal, an alkaline earth metal, a rare earth metal, a transition metal, or an earth metal.

11. The process of claim 8, wherein the olefin is isobutene and the amine product is tert-butylamine.

12. A process for preparing an amine, which comprises the steps of:
(a) reacting
  (i) an olefin with
  (ii) ammonia, a primary amine, a secondary amine or a mixture thereof,
in the presence of a borogermanate zeolite catalyst of the pentasil type at from 80° to 400° C. and under 40 to 700 bar;
(b) isolating the amine product; and
(c) recycling unreacted materials (i) and (ii).

13. The process of claim 12, wherein the reaction is carried out at from 250° to 350° C. and under 200 to 300 bar.

14. The process of claim 13, wherein the olefin is isobutylene and the amine product is tert-butylamine.

* * * * *